(12) United States Patent
Berenschot et al.

(10) Patent No.: US 9,597,490 B2
(45) Date of Patent: Mar. 21, 2017

(54) MICRONEEDLE, MICRONEEDLE ARRAY AND PRODUCTION METHOD THEREFOR

(75) Inventors: Johan Willem Berenschot, Ratum (NL); Jeroen Mathijn Wissink, Enschede (NL); Niels Roelof Tas, Enschede (NL); Meint Jelle DeBoer, Enschede (NL)

(73) Assignee: U-NEEDLE HOLDING B.V., Enschede (NL)

( * ) Notice: Subject to any disclaimer, the term of this patent is extended or adjusted under 35 U.S.C. 154(b) by 474 days.

(21) Appl. No.: 13/001,349

(22) PCT Filed: Jun. 24, 2009

(86) PCT No.: PCT/NL2009/000140
§ 371 (c)(1),
(2), (4) Date: Apr. 1, 2011

(87) PCT Pub. No.: WO2009/157765
PCT Pub. Date: Dec. 30, 2009

(65) Prior Publication Data
US 2011/0172605 A1 Jul. 14, 2011

(30) Foreign Application Priority Data

Jun. 24, 2008 (NL) .................................... 2001718

(51) Int. Cl.
*A61M 37/00* (2006.01)
(52) U.S. Cl.
CPC ... *A61M 37/0015* (2013.01); *A61M 2037/003* (2013.01); *A61M 2037/0046* (2013.01); *A61M 2037/0053* (2013.01); *B81B 2201/055* (2013.01)

(58) Field of Classification Search
CPC .... A61M 2037/003; A61M 2037/0046; A61M 2037/0053; A61M 37/0015; B81B 2201/055
(Continued)

(56) References Cited

U.S. PATENT DOCUMENTS

| 5,591,139 A | 1/1997 | Lin et al. |
| 5,928,207 A | 7/1999 | Pisano et al. |

(Continued)

FOREIGN PATENT DOCUMENTS

| JP | 2001509399 | 7/2001 |
| JP | 2002239014 | 8/2002 |

(Continued)

OTHER PUBLICATIONS

Kendal, Vertical Etching of Silicon at very High Aspect Ratios, 1979, Ann Rev Mater Sci, vol. 9, pp. 373-403.*

(Continued)

*Primary Examiner* — Imani Hayman
(74) *Attorney, Agent, or Firm* — McGuireWoods LLP

(57) ABSTRACT

The present invention provides a microneedle, comprising a shaft of a monocrystalline material having at least three walls which are formed by a crystal plane of the monocrystalline material; and a tip connected to an end of the shaft comprising at least three walls which are formed by a crystal plane of the material. The material is preferably silicon. Two of the walls of the tip are formed by the same crystal planes as two walls of the shaft. These two walls are formed by a <111> crystal plane. Preferably, three walls of the tip are formed by a <111> crystal plane.

17 Claims, 6 Drawing Sheets

(58) Field of Classification Search
USPC .............. 604/173, 272; 216/2; 438/706, 719
See application file for complete search history.

(56) References Cited

U.S. PATENT DOCUMENTS

| 8,377,364 | B2* | 2/2013 | Shiomitsu et al. ........... 264/337 |
| 2003/0078549 | A1 | 4/2003 | Stupar |
| 2007/0060837 | A1 | 3/2007 | Cho |
| 2009/0093776 | A1* | 4/2009 | Yue .................... A61B 17/3211 604/272 |

FOREIGN PATENT DOCUMENTS

| JP | 2004538106 | 12/2004 |
| JP | 2006334225 | 12/2006 |
| JP | 2006341089 | 12/2006 |
| JP | 2008 035874 | 2/2008 |
| KR | 2002 0081743 | 10/2002 |
| WO | WO 2006 055844 | 5/2006 |

OTHER PUBLICATIONS

International Search Report in connection with PCT/NL2009/000140, filed Jun. 24, 2009.
Aoyagi S. et al.: "Biodegradable Polymer Needle Having a Trench for Collecting Blood by Capillary Force", Micro Electro Mechanical Systems, 2006. MEMS 2006 Istanbul. 19$^{th}$ IEEE International Conference on Istanbul, Turkey Jan. 22-26, 2006, Piscataway, NJ, USA, IEEE LNKD—DOI:10.1109/MEMSYS.2006.1627833, Jan. 22, 2006 (Jan. 22, 2006), pp. 450-453, XP010914279, ISBN: 978-0-7803-9475-9, p. 452, paragraphs 1, 2, figures 2,7,8.
Chin-Chun Hsu et al: "Fabrication of Microneedles", Nano/Micro Engineered and Molecular Systems, 2007. NEMS '07. 2$^{nd}$ IEEE International Conference on, IEEE, Piscataway, NJ, USA, Jan. 1, 2007 (Jan. 1, 2007), pp. 639-642, XP031079825, ISBN: 978-1-4244-0610-4, the whole document.
David Mills et al.: "Non-lithographic method of forming ordered arrays of silicon pillars and macropores; Formation of Si pillars", Journal of Physics D. Applied Physics, IOP Publishing, Bristol, GB LINKD-DOI: 10.1088/0022-3727/38/4/017, vol. 38, No. 4, Feb. 21, 2005 (Feb. 21, 2005), pp. 632-636, XP020083548 ISSN: 0022-3727, *abstract, p. 634, col. 2, paragraph 2-p. 635, col. 1, paragraph 1, figures 3, 4.
Shikida M et al: "Non-photolithographic pattern transfer for fabricating arrayed three-dimensional microstructures by chemical antisotrophic etching", Sensors and Actuators A, Elsevier Sequoia S.A., Lausanne, CH LINKD-DOI: 10.1016/J.SNA.2004.04.031, vol. 116, No. 2, Oct. 15, 2004 (Oct. 15, 2004), pp. 264-271, XP004565666, ISSN: 0924-4247, the whole document.
Octrooicentrum Nederland: Rapport Betreffende Het Onderzoek Naar De stand Van De Techniek (Google translation: Netherland Patent Office: Report Regarding the Investigation into the State of the Art), dated Apr. 6, 2009.
Lye W-K en Reed M L, "Microsystems for Drug and Gene Delivery", Proceedings of the IEEE, IEEE, New York, Jan. 1, 2004, *Paragrappf A getiteld "In plane microneedles"*.
KR 20020081743 A (Digital Bio Technology), Oct. 30, 2002, *Epodoc en WPI samenvattingen*, * figuren*.
CN Office Action of Oct. 12, 2013.
Chin-Chun Hsu et al,; "Fabrication of Microneedles"; Proceedings of the 2nd IEEE International Conference on Nano/Micro Engineered and Molecular Systems; Jan. 16-19, 2007, p. 639-642.
Seung-Joon Paik, et al; In-Plane single-crystal-silicon microneedles for minimally invasive microfluid systems, Sensors and Actuators A, 2004, vol. 114, p. 276-284.
Sangeetha Swaminathan; Fabrication of Nano-Injection Needles for Neural Pathway Study in Mice, Master Theses of University of Tennessee, 2007.
Masayoshi Esashi; Overview Report, Micromachine, Applied Physics, Japan Society of Applied Physics, 1991, vol. 60, No. 3 (English Translation Not Provided).

* cited by examiner

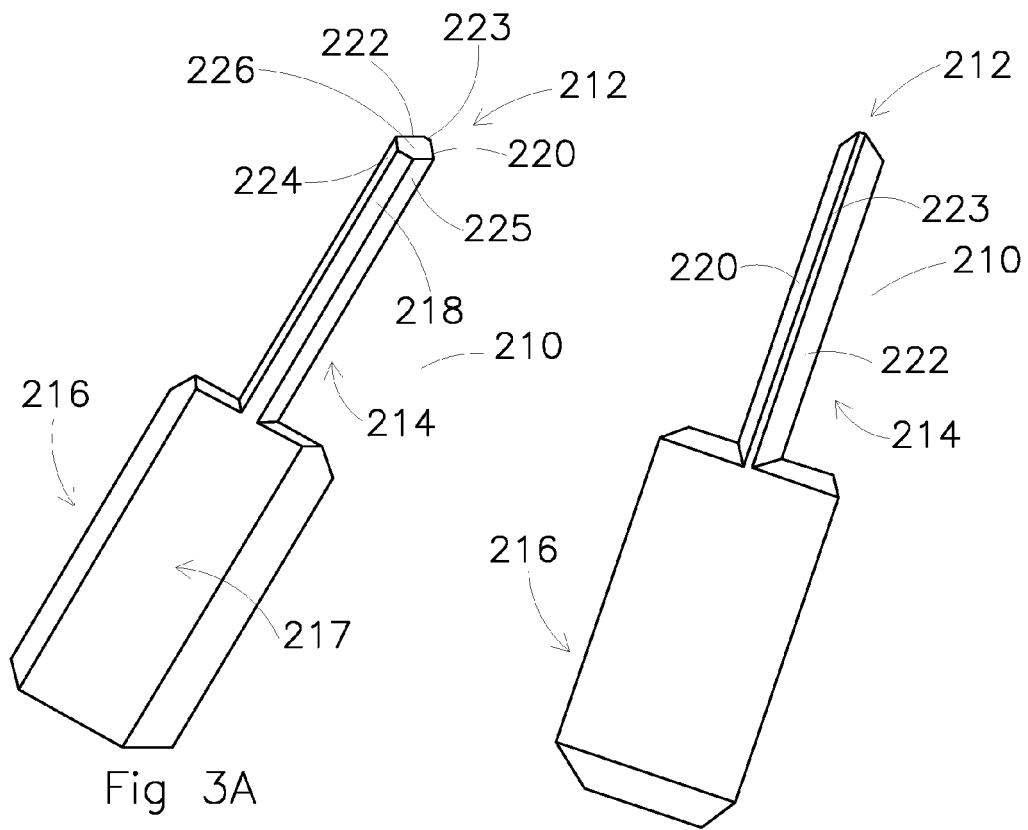
Fig 3A
Fig 3B
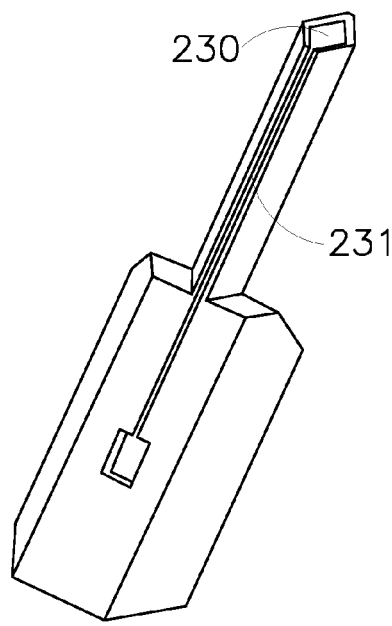
Fig 3C

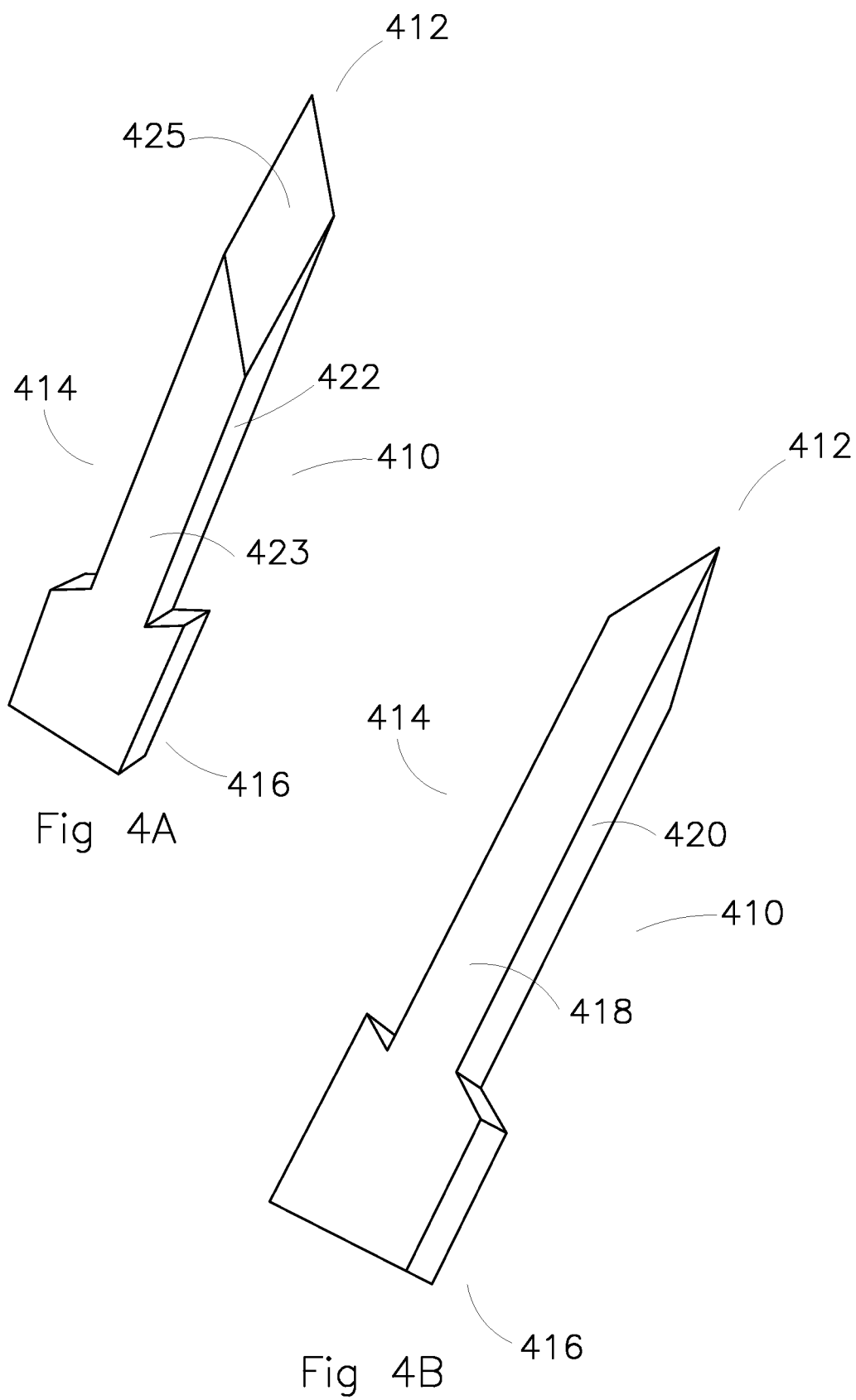

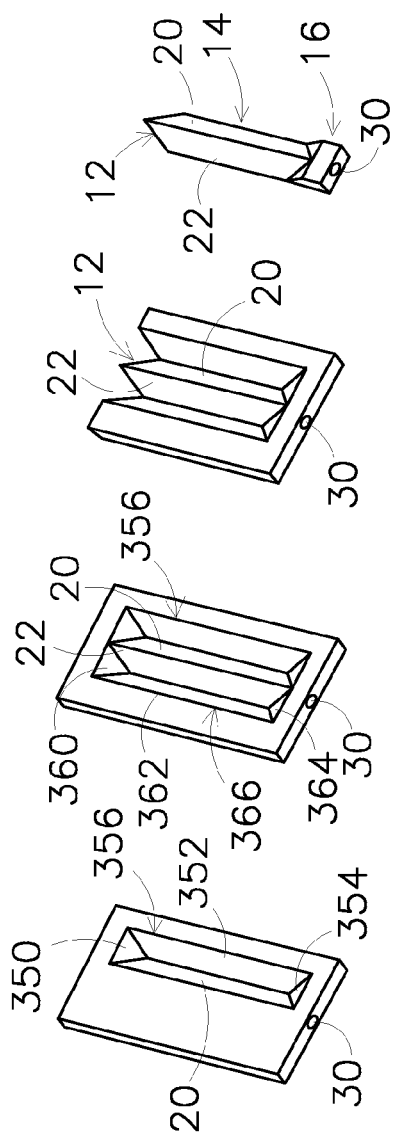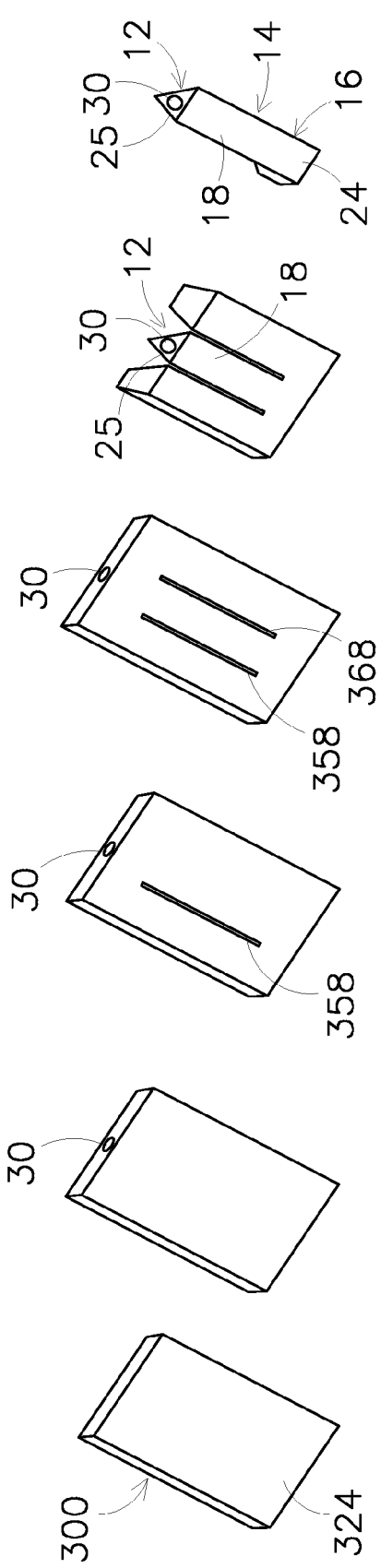

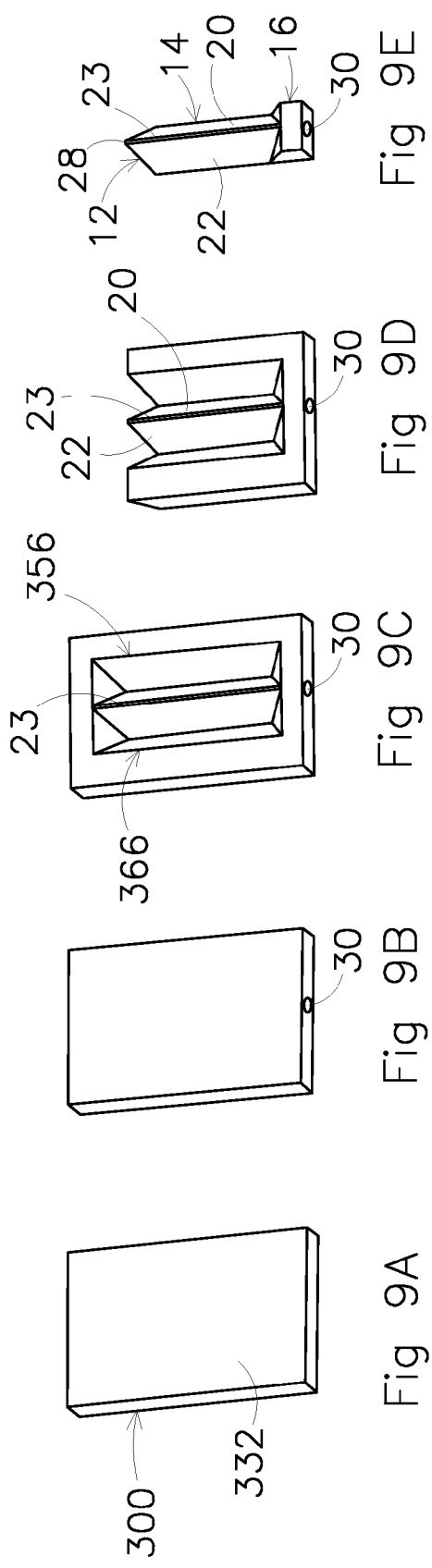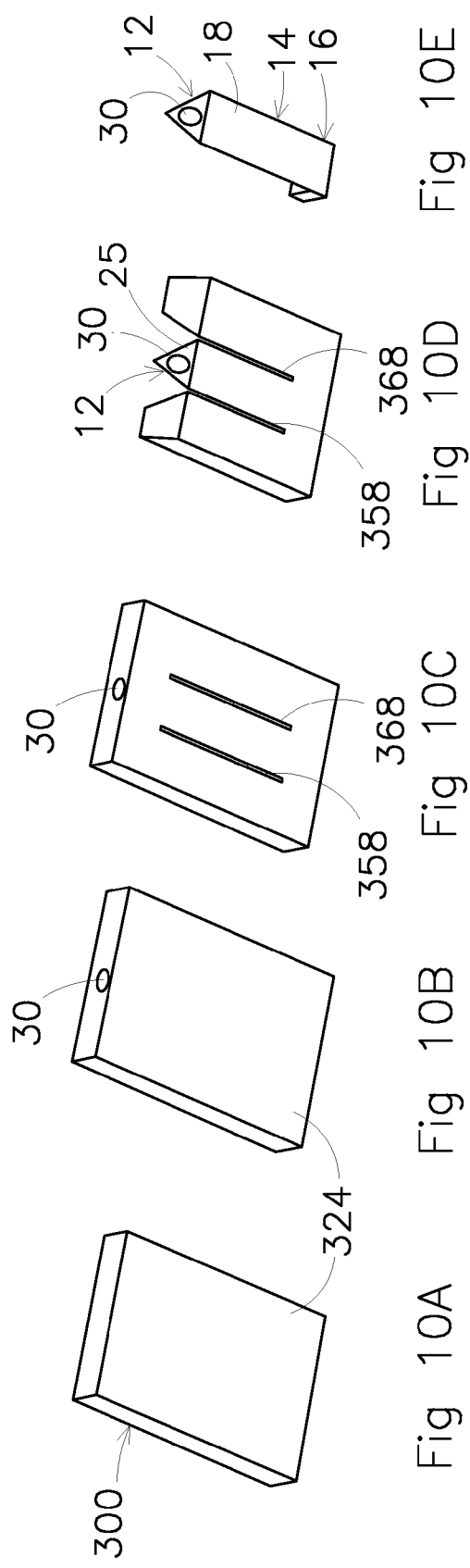

MICRONEEDLE, MICRONEEDLE ARRAY AND PRODUCTION METHOD THEREFOR

CROSS-REFERENCE TO RELATED APPLICATIONS

The present application is a National Stage entry under 35 U.S.C. §371 of international Patent Application No. PCT/NL2009/000140, filed on Jun. 24, 2009, which claims priority of Dutch Patent Application No. NL2001718, filed on Jun. 24, 2008. The disclosures of PCT/NL20091000140 and NL2001718 are hereby incorporated by reference in their entirety.

BACKGROUND OF THE INVENTION

The present invention relates to a microneedle, to a microneedle array and to a method for the production thereof.

Microneedles are a promising alternative and addition to standard injection needles. Microneedles have dimensions which are in the order of magnitude of several tens to several hundreds of micrometers. Details of the microneedle, such as the tip, have dimensions, for example, of several micrometers to one or more nanometers. As a result of their relatively small dimensions, microneedles are intended to penetrate the skin essentially painlessly and without visibly damaging the skin. The needles are preferably as sharp as possible in order to minimize the feeling of being injected by keeping the force required to push the needle into the skin as small as possible, as a result of which the skin deforms as little as possible upon injection. By selecting the length of the microneedles, medicinal products and the like can be introduced at a predetermined depth below the surface of the skin.

Microneedles can be produced using production techniques which are known for the processing of semiconductors. As described in the article "Penetration-Enhanced Ultrasharp Microneedles and Prediction on Skin Interaction for Efficient Transdermal Drug Delivery" by N. Roxhed et al., Journal of Microelectromechanical Systems, vol. 16, no. 6, December 2007, microneedles are divided into two classes, based on the production techniques used. The first class is formed by needles which extend at right angles from the plane of the substrate (out-of-plane needles). The second class is formed by needles which extend approximately parallel to the plane of the substrate (in-plane needles). Since the needles are small, a number of microneedles are preferably used simultaneously for the injection of medicinal products. However, in practice it has proven difficult to produce two-dimensional arrays of in-plane needles.

Microneedles are divided further into hollow and solid microneedles. Solid microneedles can be used, for example, to introduce a medicinal product which has been applied to the surface of the needles beforehand as a coating layer. Hollow microneedles are provided with a passage or channel, so that the medicinal products can be introduced into or under the skin through the channel of the needle.

U.S. Pat. No. 6,533,949 B1 provides a method for producing hollow out-of-plane microneedles on a silicon substrate. The needles are formed by etching an approximately V-shaped slot into the surface of the substrate. Inside the V shape a hole is also etched. The V shape may be rounded. The hole and the slot are then passivated by providing them with a protective layer. After the protective layer has been applied, the surface of the substrate is etched by means of a selective anisotropical etching process. During this process, the silicon is selectively removed from the surface of the substrate, with a protuberance remaining along a <111> crystal plane remaining inside the slot. Following subsequent removal of the protective layers, the protuberances provided with the apertures therein form microneedles.

However, due to the etching process used, the circumference of the needles formed in accordance with the process of U.S. Pat. No. 6,533,949 B1 is uneven, as a result of which the skin is damaged when the microneedles are pushed into the skin. The unevenness of the circumference can be seen, for example, in FIG. 4 of the article "Silicon Micromachined Hollow Microneedles for Transdermal Liquid Transport", Journal of Microelectromechanical Systems, vol. 12, no. 6, December 2003. In addition, the length and sharpness of the microneedles is limited by the production process. As a result of the limited length and/or sharpness of the needles, not all needles of an array penetrate the skin, which may result in leaks, that is to say that when liquid is used, this leaks away via the needles which have not penetrated the skin.

U.S. Pat. No. 5,928,207 provides an in-plane microneedle, comprising an elongate shaft which ends in a tip. The walls of the shaft are etched isotropically or anisotropically, while the tip has been etched isotropically. As a result of isotropical etching, the tip has a sharp end which is much flatter and narrower than the shaft. At the top side of the needle, the transition from the tip to the shaft is relatively abrupt, however, as a result of which said transition damages the skin when the needle penetrates it.

In addition to the above, all hitherto known microneedles in practice appear to have a sharpness which is at most comparable to the sharpness of a standard 30G injection needle, as supplied by Popper & Sons, Inc., N.Y. (USA). However, the sharpness of a 30G injection needle is not sufficient to prevent damage to the skin. In use, (a part of) the microneedle is pushed into the skin with a certain force, resulting in a 'needle trauma' and the injection can be felt. The skin is damaged, red and/or sensitive after the injection. In addition, the sharpness is insufficient for use on relatively soft skin, such as the skin on the underarm or the face of a human being.

SUMMARY OF THE INVENTION

It is an object of the present invention to provide a sharper microneedle.

This object is achieved according to the invention by means of an in-plane microneedle made from a monocrystalline material, comprising:

a shaft of the monocrystalline material having at least two walls which are formed by a relatively slow etching crystal plane of the material; and a tip connected to an end of the shaft and comprising at least three was which are formed by a relatively slow etching crystal plane of the monocrystalline material.

The tip is thus formed by slowly etching crystal planes of the monocrystalline material. As a result of the production process, the crystal planes may be approximately atomically flat, as a result of which the friction between the microneedle and the skin is minimal. The lines or edges where the crystal planes of the tip adjoin one another are sharp, that is to say the radius of curvature thereof is, for example, smaller than 10 μm, up to the order of magnitude of the atomic radius of curvature. The end of the tip, where the crystal planes converge, is also sharp and has a radius of curvature which is, for example, smaller than 10 μm. The lines of intersection of the crystal planes furthermore ensure that the tip penetrates into the skin along its entire length. As a result of the cutting of the tip, a smaller force is required to push the microneedle into the skin. The shaft then slides into the hole which has been cut into the skin by the tip. With the exception of a hollow inner side which may optionally be provided, the microneedle can be produced completely by anisotropic wet-etching. Final processing such as grinding etc, is superfluous.

Preferably, the monocrystalline material is silicon, as the production techniques for silicon are present. In addition, silicon is a relatively inexpensive semiconductor which is available in large quantities.

In one embodiment, two of the walls of the tip are formed by the same crystal planes as two walls of the shaft. The two crystal planes together form a V-shaped profile which extends along the length of the tip and the shaft. Both the shaft and the tip of the microneedle thus have a cutting effect on the skin. The force to push the needle into the skin is thus smaller and damage to the skin is limited to an incision with dimensions which correspond to the circumference of the microneedle.

In another embodiment, the two walls of the tip, which are formed by the same crystal planes as the two walls of the shaft, are formed by a relatively slow etching crystal plane. The crystal planes adjoin at a suitable sharp angle in order to achieve the desired cutting action.

In yet another embodiment, three walls of the tip, which are formed by a relatively slow etching crystal plane, are formed by a <111> crystal plane. The three walls converge at one end of the tip in an atomically sharp manner. In this case, the three walls adjoin one another at an internal angle of approximately 70.53°. The previous characteristics contribute to the sharpness of the tip. The approximately atomically flat crystal planes minimize the friction between the tip and the skin when using the microneedle. The crystal planes adjoin one another at an internal acute angle.

Preferably, a channel is arranged in the shaft and/or the tip. The channel is, for example, a buried channel or an open channel.

According to another aspect, the invention provides a microneedle array, comprising:
  a holder which is provided with an approximately flat end;
  one or more microneedles which are fitted in the end of the holder.

The one or more microneedles comprise, for example, the above-described microneedle. The microneedle array according to the invention makes it possible to use an arbitrary number of in-plane microneedles in an arbitrary two-dimensional configuration. As described in the article mentioned in the introduction by N. Roxhed et al., in-plane microneedles have hitherto hardly been used, if at all, since it was only possible to use a single row of microneedles at most. Since in-plane microneedles can comprise a shaft, the length thereof can be selected arbitrarily, so that deeper penetration of the skin is possible than with out-of-plane microneedles.

Preferably, the holder comprises a thermoplastic. The holder comprises, for example, a cylindrical holder, which is provided with a flat and circular end. Apertures are provided in the end at the locations which are intended for the microneedles. The microneedles are, for example, fused into the apertures by heating the microneedles. To this end, the holder is preferably made from a thermoplastic, such as PE, PP and/or POM.

According to another aspect, the invention provides a method for the production of a microneedle as described above.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings:

FIG. 1b shows a perspective top view of the microneedle from FIG. 1a;

FIG. 2b shows a perspective top view of the microneedle from FIG. 2a;

FIG. 3a shows a perspective bottom view of yet another embodiment of a microneedle according to the invention;

FIG. 3b shows a perspective top view of the microneedle from FIG. 3a;

FIG. 3c shows a perspective bottom view of a variant of the microneedle from FIG. 3a;

FIG. 4a shows a perspective bottom view of yet another embodiment of a microneedle according to the invention;

FIG. 4b shows a perspective top view of the microneedle from FIG. 4a;

FIGS. 7A to 7F show perspective top views of successive process steps for the production of the microneedle from FIG. 1;

FIGS. 8A to 8F show perspective bottom views which correspond to the process steps of FIGS. 7A to 7F;

FIGS. 9A to 9E show perspective top views of successive process steps for the production of another embodiment of a microneedle; and FIGS. 10A to 10E show perspective bottom views which correspond to the process steps of FIGS. 9A to 9E.

DETAILED DESCRIPTION OF THE INVENTION

Figure 1A:
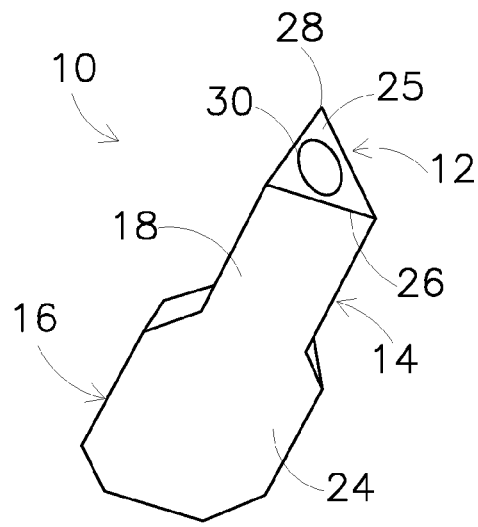
FIG. 1a shows a perspective bottom view of an embodiment of a microneedle according to the invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parks throughout the several views of the drawings.

Figure 1B:
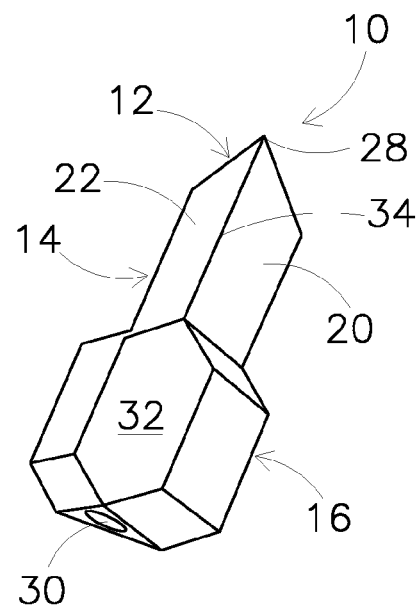

In an embodiment shown in FIGS. 1a and 1b, a microneedle 10 is formed from a substrate of monocrystalline silicon <100>. The microneedle 10 comprises a tip 12 which is integrally formed with a shaft 14. Optionally, an opposite end of the shaft is provided with a widened section or base 16. The base 16 serves, for example, to handle the microneedle and/or to couple it to other elements, see for example FIG. 5. To this end, the base can have any desired shape and will therefore not be described in any more detail.

The shaft 14 has a shape which is approximately triangular in cross section, having at least three walls 18, 20, 22 which adjoin one another. The plane 18, just like the plane 24 of the base 16, corresponds to a surface of the substrate and is, in the illustrated embodiment, thus a <100> crystal plane. The planes 20 and 22 are <111> crystal planes of the silicon.

The tip 12 comprises three adjoining walls 20, 22 and 25. The planes 20 and 22 also form a side wall of the shaft. The plane 25 is a <111> crystal plane which, from a line of intersection 26 with the plane 18, extends obliquely in the direction of a pointed end 28 of the tip 12. The outer circumference of the shaft 14 has a cross section which is equal to the cross section of the widest part of the tip 12, at the location of the line of intersection 26.

Optionally, a channel 30 is provided in the microneedle 10, through which for example medicinal products and liquids can be transported.

A plane 32 of the base, which plane 32 is opposite the plane 24, also forms part of the surface of the substrate. Thus, the plane 32 is a <100> plane. The plane 25 is at an internal angle with respect to the plane 32 of approximately 54.74°, and also with respect to the line of intersection 34 of the walls 20, 22.

Figure 2A:
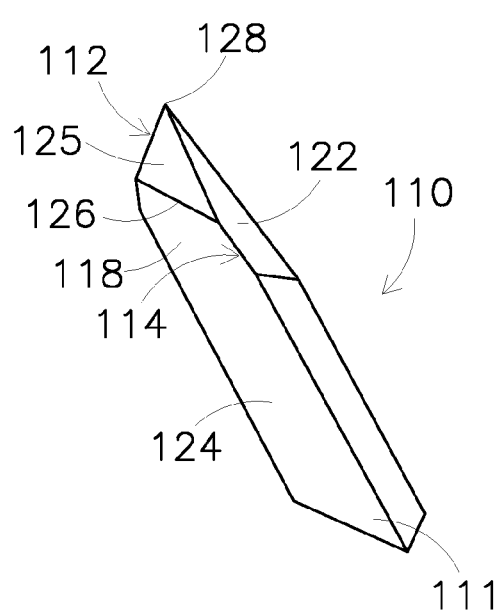
FIG. 2a shows a perspective bottom view of another embodiment of a microneedle according to the invention.
Figure 2B:
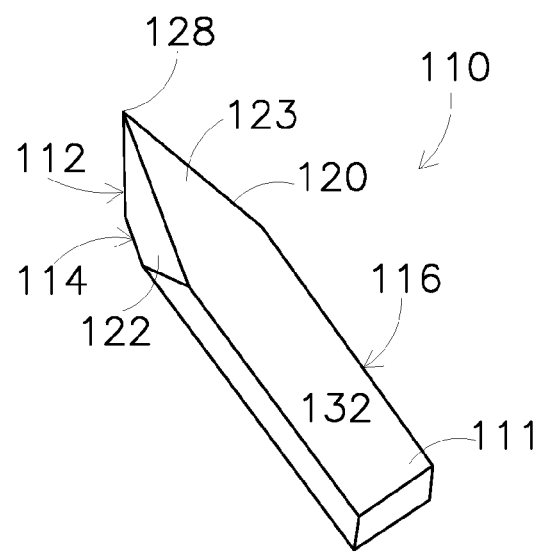

In another embodiment shown in FIGS. 2a and 2b, a microneedle 110 is formed from a substrate of monocrystalline silicon <211>. The microneedle 110 comprises a tip 112 which is integrally formed with a shaft 114. As the microneedle 110 is still connected to a remainder of the substrate 111 from which the microneedle is produced, the shaft can still be provided with a base 116. Within the limits formed by the planes 124, 132 of the substrate 111, the base may be given any shape which is possible by microproduction.

In cross section, the shaft 114 is approximately trapezium-shaped. In top or bottom view, the shaft 114 widens, viewed from the dividing iine 126 with the tip 112. The shaft 114 comprises four walls 118, 120,122 and 123. The walls 118 and 123 correspond to surfaces of the substrate and, in the present embodiment, are <211> crystal planes. The walls 120, 122 are <111> crystal planes which are at an angle with respect to the walls 118, 123.

The tip 112 comprises three adjoining walls 120, 122, 125 and a part of the wall 123. The walls 120 and 122 also form a side wall of the shaft. The plane 125 is a <111> crystal plane which, from a line of intersection 126 with the plane 118, extends obliquely in the direction of a pointed end 128 of the tip 112. The wall 125 is at an internal angle of approximately 19.47° to the wall 123. This angle can therefore be chosen by using a substrate having a certain crystal orientation at the surface as starting material.

In order that it can be used, the microneedle 110 shown in FIGS. 2a and 2b will be released from the substrate again.

In an embodiment shown in FIGS. 3a and 3b, a microneedle 210 is formed from a substrate of monocrystalline silicon <100>. The microneedle 210 comprises a tip 212 which is integrally formed with a shaft 214. Optionally, an opposite end of the shaft is provided with a widened section or base 216. The base 216 serves, for example, to handle the microneedle and/or to couple it to other elements, see for example FIG. 5. The base will not be described.

In cross section, the shaft 214 approximately has the shape of a pentagon, with walls 218, 220, 222, 223, 224 and 225, which adjoin one another. Just like plane 217 of the base 216, plane 218 corresponds to a surface of the substrate and, in the illustrated embodiment, is thus a <100> crystal plane. The plane 223 is also a <100> crystal plane and is situated parallel to 218. The planes 225, 220, 222, 224 and 226 are <111> crystal planes of the silicon.

The tip 212 comprises the walls 218, 220, 222, 223, 224, 225 and 226. The plane 226 is a <111> crystal plane which adjoins the planes 218, 225, 220, 223, 222, 224 and, from a line of intersection with the plane 218, extends obliquely in the direction of a pointed end, where it adjoins wall 223.

An advantage of this embodiment may be that the needle has an advantageous circumference relative to the cross section. As a result thereof, the required force of penetration for a certain channel size with a certain circulation is limited. In addition, the cut in the skin which a microneedle according to this embodiment causes, is also limited.

FIG. 3c shows how a channel 230 may optionally be arranged in the microneedle 210, through which, for example medicinal products and liquids can be transported. The channel 230 may have a diamond-shaped cross section and may be connected to a slot 231. This slot 231 can both be left open, as illustrated, or be closed by means of the Buried Channel Technology of M. J. De Boer, JOURNAL OF MICROELECTROMECHANICAL SYSTEMS, VOL. 9, NO. 1, MARCH 2000. If the channel is left open, in other words if the slot is not closed, the channel remains open in the longitudinal direction. Even with an open channel, liquid can be injected into the skin, as the skin closes the channel when the microneedle is inserted completely into the skin.

In another embodiment shown in FIGS. 4a and 4b, a microneedle 410 is formed from a substrate of monocrystalline silicon <110>. The microneedle 410 comprises a tip 412 which is integrally formed with a shaft 414. The shaft 414 may be provided with a base 416. In cross section, the shaft 414 approximately has the shape of a square.

The shaft 414 comprises four walls 418, 420, 422 and 423. The walls 418 and 423 correspond to surfaces of the substrate and, in the present embodiment, are <110> crystal planes. In the present embodiment, the walls 420 and 422 are slow-etching <111> crystal planes.

The tip 412 comprises five walls 418, 420, 422, 423 and 425 adjoining each other, i.e. all planes of the shaft, and the <111> plane 425. The walls 420 and 422 are slow-etching <111> planes and also form a side wall of the shaft. The plane 425 is a <111> crystal plane which, from a line of intersection with the plane 422, extends obliquely in the direction of a pointed end of tip 412.

It may be an advantage of this embodiment that the microneedle has a relatively small aperture angle, as a result of which the required force of penetration is smaller than with needles having relatively large angles. In this context, this is referred to as a sharper needle or tip.

Since the above-described microneedles are in-plane needles, see FIGS. 7-10, the invention provides a way to use an arbitrary number of microneedles simultaneously in an arbitrary two-dimensional configuration.

Figure 5:
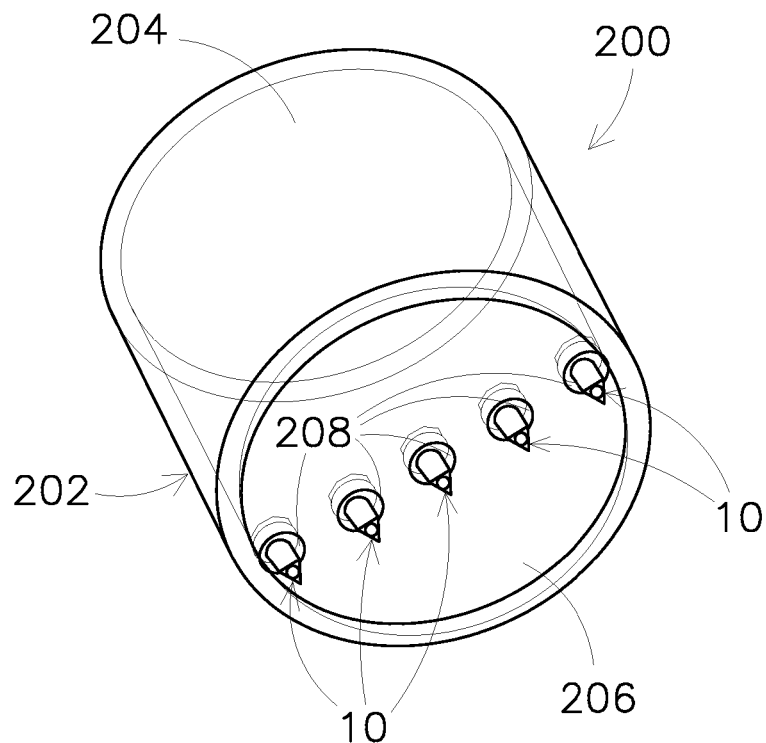
FIG. 5 shows a perspective bottom view of an embodiment of a microneedle array according to the invention.
Figure 6:
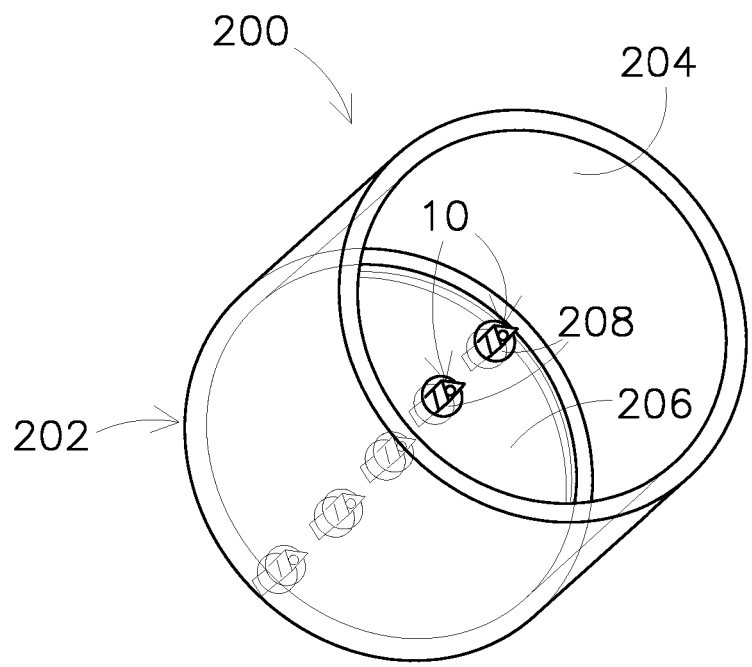
FIG. 6 shows a perspective top view of the microneedle array from FIG. 5.

FIGS. 5 and 6 show a microneedle array 200, comprising a holder 202 which is provided with a cylindrical wall 204 having an approximately circular flat end 206. The end 206 has an aperture 208 at each location where a microneedle is desired. Each aperture 208 has, for example, a microneedle 10. By way of example, the microneedle 10 from FIG. 1a is shown, but any other desired microneedle can also be arranged in an aperture 208. In addition, a different microneedle can be fitted per aperture 208, for example of a different length. Since in-plane microneedles may comprise a shaft, the length thereof may be chosen arbitrarily, so that deeper penetration of the skin is possible than with out-of-plane microneedles.

Preferably, the holder 202 comprises a thermoplastic, such as PE and/or PP. The microneedles are, for example, fused into the apertures. Fusing can be achieved by heating a microneedle until the plastic of the holder melts locally around the aperture in which the microneedle is arranged. By then allowing the respective microneedle to cool down, the molten plastic sets again and forms a water-tight and air-tight connection between the microneedle and the holder. A microneedle may, for example, be heated in a contactless manner by means of a light or laser beam focussed on the microneedle. By heating the microneedles contactlessly, assembly is significantly simplified and the risk of damage is minimized.

The production of the above-described microneedles is described below. In the description, the terms which are customary in the processing of a semiconductor material such as silicon are used. For a detailed description of the terms used, reference is made to "Silicon Micromachining" by M. Elwenspoek, H. V. Jansen, Cambridge University Press 1998.

The microneedle according to the present invention is made from a substrate of monocrystalline material, for example a semiconductor, having surfaces which correspond to a certain crystal plane. The shape of the microneedle depends on the orientation of the crystal planes in the substrate. The present invention provides a sharper microneedle by etching free certain crystal planes in monocrystalline substrates with a certain orientation.

The (two-dimensional (2D) photolithographic) production techniques used in this invention are based on the monocrystalline substrates. The substrates are sawn from a bulk material which essentially comprises a single crystal. Usually, the substrate is a round disc or a wafer. The plane which results on the surface of the substrate after sawing determines the crystal direction with respect to the surface of the substrate. Since the surface of the substrate is determined by the direction of sawing, the crystal plane at the surface of the substrate can be chosen arbitrarily with respect to the crystal direction in the substrate. This surface is usually a crystal plane. The crystal plane is referred to by Miller indices, e.g. a <100>, <110>, <111> plane. A crystal plane is any plane in the crystal in which the atoms form a repeating pattern. A substrate is inter alia referred to by the crystal plane of the surface, for example a <100> oriented silicon substrate, or simply <100> silicon or silicon <100>. Any other arbitrary crystal plane, such as <211> or <310> is also possible, however.

The choice of crystal plane for the surface of the substrate partly determines the internal angles of the tip of the microneedle.

Operations are carried out on the surfaces of the substrates, for example making lithographic images, etching material away and depositing material, as a result of which structures are created on the substrate surface and/or in the bulk of the substrate.

The monocrystalline substrates comprise crystal planes which may have mutually different etching speeds, so-called anisotropic etching processes. Relatively slow etching crystal planes thus form atomically flat crystal planes during anisotropic etching processes. As a result of a particular selection and sequence of the 2D lithographic steps and etching processes, examples of which are given, but to which the invention is not limited, these crystal planes form the atomically flat walls of a microneedle according to the present invention.

The surfaces of the substrates are finished by mechanical and/or chemical polishing in order to ensure a certain degree of flatness. This surface is usually not slow etching, but by the finishing treatment of the surface of the substrate, the latter is usually flat to atomically flat, at least atomic flatness can be approached.

Both the top and the bottom side of a substrate can be polished. Substrates are also designated thereby and the degree of flatness may also be designated.

Monocrystalline silicon is the material which is preferred, but the invention is not limited to silicon. Monocrystalline silicon forms a cubic crystal, in which the atoms form a structure or a tetrahedron which is comparable to diamond. Other suitable substrates comprise, for example, a monocrystalline semiconductor or quartz.

FIGS. 7 to 10 illustrate the production of a microneedle starting from a silicon <100> substrate, that is to say that a microneedle will be obtained approximately as shown in FIGS. 1a and 1b. Using the same production steps, but starting from silicon with a different orientation of the substrate and with a lithographic design (design of the two-dimensional mask) which is adapted to said orientation, other microneedles can be obtained, see for example FIGS. 2a and 2b. The smallest internal angle of the tip may in this case be smaller, because the smallest angle between the crystal plane on the substrate surface (<211>) and the relatively slow etching planes (<111>) is smaller. The smallest angle is approximately 20 degrees with <211> (the angle between the <211> surface of the substrate and a <111> plane) instead of approximately 55 degrees with <100> (the angle between the <100> plane and a <111> plane). However, the material of the substrate is in all cases the same monocrystalline material. A substrate which comprises a semiconductor can, if desired, be p-doped or n-doped.

In one embodiment (FIGS. 7A, 8A), the starting material is a substrate 300 which is provided with a passivating layer on all sides. A passivating layer is a protective layer which is resistant to etching agents for the material of the substrate, such as silicon. The passivating or protective layer comprises, for example, silicon nitride or silicon dioxide. As mentioned, the substrate is made of <100> silicon, so that the surfaces 324 and 332 are a <100> crystal plane.

In a first step, a buried channel 30 is provided at the location where a microneedle is to be produced (FIGS. 7B, 8B). It is also possible to provide the buried channel 30 during, after or before other steps. For a description of process steps for providing a buried channel in a semiconductor substrate, reference is made to "Micromachining of Buried Micro Channels in Silicon" by Meint J. de Boer et al., Journal of Microelectromechanical Systems, Vol. 9, No. 1, March 2000. In said article, for example, table 1 describes four possible processes for providing a buried channel in the substrate. Depending on the chosen substrate (for example p- or n-type silicon, resistance, crystal orientation), a suitable process can be chosen. According to one embodiment of the invention, the buried channel 30 remains in the substrate in order to form a passage for the eventual microneedle. It is also possible to leave the channel open, a slot being formed in the longitudinal direction of the channel, so that the channel is open in the longitudinal direction. The skin into which the microneedle is introduced then closes off the channel, as a result of which liquid can be injected through the channel.

The buried channel may be arranged on the side of the surface 324 or of the surface 332 of the substrate, as desired. However, it is preferred if the buried channel 30 is arranged on the side of the surface 324.

In a subsequent step (FIGS. 7C, 8C), a protective layer is first provided at the top of the substrate 300. In the protective layer, an elongate aperture (not shown) is provided, parallel to the buried channel 30. At the location of the aperture, the substrate is not covered. Subsequently, the substrate 300 is anisotropically etched.

Potassium hydroxide (KOH) which etches silicon selectively is a suitable anisotropic wet-etching agent. KOH is able to etch the silicon approximately 400 times more quickly in the direction of the <100> crystal planes than in the direction of the <111> planes. In other words, the <111> planes etch more slowly than other crystal planes. Another suitable etching agent is EDP (an aqueous solution of ethylene diamine and pyrocatechol). EDP etches p-doped silicon approximately at a ratio of 50:3 in the direction of the <100> crystal planes compared to the direction of the <111> planes. Tetramethylammoniumhydroxide (TMAH) can also be used, but the selectivity between <100> and <111> planes is worse than that of EDP. Since KOH etches most selectively, it is preferred for the present invention.

The etching agent etches away the silicon through the aperture in the protective layer, in which process the relatively slow etching <111> planes become visible. The etching step is terminated as soon as the protective layer on the other side 324 of the substrate is reached. The <111> crystal planes 20, 350, 352, and 354 together form an elongate well 356 in the substrate (FIG. 7C), a slot or aperture 358 having been produced at the bottom of the well (FIG. 8C) in the substrate. The slot 358 is closed, that is to say not open, by a membrane which is formed by the remainder of the protective layer.

In a next step (FIGS. 7D, 8D), a protective layer is first provided at the top of substrate 300. In the protective layer, an elongate aperture (not shown) is provided next to the well 356, on the other side of the buried channel 30. At the location of the aperture, the substrate is not covered. Subsequently, the substrate 300 is anisotropically etched.

The etching agent etches away the silicon through the aperture in the protective layer, in which process the relatively slow etching <111> planes become visible. The etching step is terminated as soon as the protective layer on the other side 324 of the substrate is reached. The <111> crystal planes 22, 360, 362, and 364 together form an elongate well 366 in the substrate (FIG. 7D), a slot or aperture 368 (FIG. 8D) having been produced at the bottom of the well in the substrate. The slot 368 is closed, that is to say not open, by a membrane which is formed by the remainder of the protective layer.

In a next step (FIGS. 7E, 8E), a protective layer is first provided at the top of the substrate. In the protective layer, an aperture (not shown) is provided on the bottom side 324 of the substrate, where the substrate is not covered for etching the tip 12. Subsequently, the silicon of the substrate is anisotropically etched using an etching agent (for example KOH) through the aperture, in which process the relatively slow etching <111> crystal plane 25 becomes visible.

In a next step (FIGS. 7F, 8F), remains of the protective layers are first removed. In addition, part of the material of the buried channel which protrudes from the tip 12 is removed in the process.

Subsequently, the microneedle 10 is detached from the substrate. The microneedle 10 can for example be removed from the substrate by etching (result shown in FIGS. 1a and 1b), by sawing (result shown in FIGS. 7F, 8F), or by breaking.

In the case of etching, a protective layer is first provided at the top of the substrate. In the protective layer, an aperture (not shown) is provided on the bottom side 324 or the top side 332 of the substrate where the substrate is not covered for etching the base 16. Thereafter, an etching agent (for example KOH) is used to anisotropically etch the silicon of the substrate through the aperture until the base 16 remains.

Another, more simple method for producing a microneedle according to the invention is shown in FIGS. 9 and 10.

The steps shown in FIGS. 9A, 9B, 9D, 9E are the same as the steps described above with reference to FIGS. 7A, 7B, 7E, 7F, respectively. The buried channel 30 can be arranged on the side of the surface 324 or of the surface 332 of the substrate, as desired. However, it is preferred if the buried channel 30 is provided on the side of the surface 324.

The difference relates to the step shown in FIGS. 9C, 10C. The substrate 30 is provided on all sides with a protective layer, in which, in this embodiment, two apertures are left open on either side of the buried channel. The apertures are separated by a thin strip of protective layer. The width of the strip depends on the photolithographic process which is used for defining the strip, and is for example between 1 μm and 100 μm.

Subsequently, the substrate 300 is etched anisotropically. The etching agent etches the silicon away through the two apertures in the protective layer, in which process the slow etching <111> planes become visible. The etching step is terminated as soon as the protective layer on the other side 324 of the substrate is reached. The <111> crystal planes 20, 350, 352, 354 together form the elongate well 356 in the substrate (FIG. 9C), a slot or aperture 358 (FIG. 9C) having been produced in the substrate on the bottom of the well. At the same time, next to the well 356 the well 366 was produced, formed by the <111> planes 22, 360, 362, 364. On the bottom of the well 366, the slot or aperture 368 (FIG. 9C) in the substrate has been produced. The slot 358 and the slot 368 are both closed off by a membrane which is formed by a remainder of the protective layer.

The microneedle which has been produced according to the method from FIGS. 9 and 10 comprises a plane 23 between the planes 20, 22. The plane 23 is a remainder of the surface 332 of the substrate which was present below the abovementioned strip of the protective layer during the anisotropic etching of the wells 356 and 366. The plane 23 has a width corresponding to the width of the strip, i.e. for example between approximately 1 μm and 100 μm.

The tip 12 of the microneedle which has been produced according to the method of FIGS. 9 and 10 (FIGS. 9E, 10E) is therefore surrounded by foray walls 20, 22, 23 and 25. The walls 20, 22 and 25 are <111> crystal planes of the silicon. The wall 23 is a remainder of the surface 332 of the substrate. In the illustrated embodiment, wall 23 is a <100> crystal plane.

The tip 12 according to the present invention is formed by walls which comprise crystal planes of the substrate. The walls adjoin one another at lines of intersection, and taper off into an end 28. The lines of intersection and the end are approximately atomically sharp, that is to say that the radius of curvature of the end 28 and/or of the lines of intersection between the walls 20, 22, 23 and/or 25 have a radius of curvature in the order of the radius of an atom. The radius of curvature is, for example, in the order of 1-100 nm. As a result of the small radius of curvature, the microneedle is sharp. Due to the small radius of curvature of the lines of intersection which, in addition, extend along the entire length of the tip 12, the entire tip of the microneedle cuts into the skin. Consequently, a smaller force is required to penetrate the skin than is the case with known microneedles. Since the shaft 14 also has walls of crystal planes which adjoin one another at lines of intersection, the shaft also has a cutting action on the skin. The walls 18, 20, 22, 23 and 25 of the microneedle approximately correspond to a crystal plane of the silicon, and can be approximately atomically flat. An atomically flat wall causes less friction on the skin than a rougher wall, as a result of which the microneedle according to the invention experiences less counterforce from the skin and damages the skin to a lesser degree.

An embodiment of the method for the production of a microneedle which can result in microneedles shown in FIGS. 3a and 3b is described below. The first steps may be similar to the steps described with reference to FIGS. 7A-7D/8A-8D or 9A-9D/10A-10D, in which two wells are etched on a first side of the substrate. Then, as an additional intermediate step, another, opposite side of the substrate is etched. In this case, two wells are also etched in this other side in a similar manner, so that the wells in one side of the substrate correspond to the wells on the other side of the substrate along a certain section. The subsequent steps of the method correspond to the steps as described with reference to FIGS. 7E/8E or 9E/10E.

Another method for producing a microneedle which can result in microneedles shown in FIGS. 4a and 4b starts with etching a microneedle having a square cross section from a substrate, in which the shaft comprises two sides which correspond to the <110> sides of the substrate. The two other sides are at right angles thereto and are <111> planes. Then, a part of the microneedle is anisotropically etched away, as a result of which a <111> plane forms a tip of the microneedle, as is indicated in FIGS. 4a and 4b by plane 425.

After the microneedle has been produced, a coating layer may still be applied on the outer surface thereof in order to allow the microneedle to slide into the skin more easily. The coating layer comprises, for example, a silicone oil. The silicone oil may, for example, be applied by submerging the microneedles in a bath of silicone oil. In addition, the microneedles may be taken to a chamber in which the silicone oil is then applied in vapour form or by means of a fine mist or spray.

While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications or modifications of the invention.

The invention claimed is:

1. An in-plane microneedle made from a monocrystalline material, comprising:
   a shaft, comprising at least three walls, each of the at least three walls being <111> crystal planes of the monocrystalline material; and
   a tip connected to an end of the shaft and comprising at least three walls, each of the at least three walls being <111> crystal planes of the monocrystalline material,
   wherein at least three of the walls of the tip are adjoining and at least three of the walls of the tip are formed by the same <111> crystal planes as the at least three walls of the shaft,
   wherein the tip comprises at least two cutting edges, the at least two cutting edges each being formed by lines of intersection where a pair of the <111> crystal planes of the tip adjoin one another,
   wherein said <111> crystal planes of the tip and the shaft are atomically flat, and wherein said cutting edges are atomically sharp.

2. The microneedle according to claim 1, wherein the <111> crystal planes are not parallel to one another.

3. The microneedle according to claim 2, wherein the tip comprises a fourth wall which is identical to a surface of a substrate of the monocrystalline material from which the microneedle is made.

4. The microneedle according to claim 1, wherein the microneedle is formed from a monocrystalline silicon substrate having surfaces of a crystal orientation matching the sharpness of the tip.

5. The microneedle according to claim 1, wherein the monocrystalline material is one of the following: monocrystalline silicon <100>, monocrystalline silicon <211> or monocrystalline silicon <110>.

6. The microneedle according to claim 1, wherein a channel is provided in at least one of the shaft and the tip.

7. The microneedle according to claim 6, in which the channel is open in the longitudinal direction.

8. The microneedle according to claim 1, wherein said <111> crystal planes of the tip converge into an end of the tip.

9. The microneedle according to claim 8, wherein said <111> crystal planes of the tip converge into the end of the tip in an atomically sharp manner.

10. The microneedle according to claim 8, wherein said <111> crystal planes of the tip converge into the end of the tip at an internal acute angle.

11. An in-plane microneedle made from a monocrystalline material, comprising:
    a shaft, comprising at least two walls, each of the at least two walls being <111> crystal planes of the monocrystalline material; and
    a tip connected to an end of the shaft and comprising at least three walls, each of the at least three walls being <111> crystal planes of the monocrystalline material,
    wherein the at least three walls of the tip are adjoining and the three walls of the tip converge at one end in an approximately atomically sharp manner and the at least three walls adjoin one another at an internal angle of about 70°,
    wherein the tip comprises at least two cutting edges, the at least two cutting edges each being formed by lines of intersection where a pair of the <111> crystal planes of the tip adjoin one another, wherein said <111> crystal planes of the tip and the shaft are atomically flat, and wherein said cutting edges are atomically sharp.

12. The microneedle according to claim 11, wherein the <111> crystal planes are not parallel to one another.

13. The microneedle according to claim 12, wherein the tip comprises a fourth wall which is identical to a surface of a substrate of the monocrystalline material from which the microneedle is made.

14. The microneedle according to claim 11, wherein the microneedle is formed from a monocrystalline silicon substrate having surfaces of a crystal orientation matching the sharpness of the tip.

15. The microneedle according to claim 11, wherein the monocrystalline material is one of the following: monocrystalline silicon <100>, monocrystalline silicon <211> or monocrystalline silicon <110>.

16. The microneedle according to claim 11, wherein a channel is provided in at least one of the shaft and the tip.

17. The microneedle according to claim 16, in which the channel is open in the longitudinal direction.

* * * * *